United States Patent
Woo et al.

(10) Patent No.: US 9,248,209 B2
(45) Date of Patent: Feb. 2, 2016

(54) COMPOSITIONS COMPRISING HYDROPHOBICALLY MODIFIED MALODOR CONTROL POLYMERS

(75) Inventors: Ricky Ah-Man Woo, Hamilton, OH (US); Cahit Eylem, West Chester, OH (US); Yonas Gizaw, West Chester, OH (US); Larissa Azirbayeva, Mason, OH (US); Zaiyou Liu, West Chester, OH (US); Jeffrey Scott Dupont, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 50 days.

(21) Appl. No.: 13/006,615

(22) Filed: Jan. 14, 2011

(65) Prior Publication Data

US 2012/0183488 A1    Jul. 19, 2012

(51) Int. Cl.
*A61L 9/01* (2006.01)

(52) U.S. Cl.
CPC ............... *A61L 9/01* (2013.01); *A61L 2209/21* (2013.01)

(58) Field of Classification Search
None
See application file for complete search history.

(56) References Cited

U.S. PATENT DOCUMENTS

| | | | | |
|---|---|---|---|---|
| 4,941,991 | A * | 7/1990 | Rajamannan | 252/189 |
| 5,861,144 | A * | 1/1999 | Peterson et al. | 424/65 |
| 6,103,678 | A | 8/2000 | Masschelein et al. | |
| 6,248,135 | B1 * | 6/2001 | Trinh et al. | 8/137 |
| 6,454,876 | B1 * | 9/2002 | Ochomogo et al. | 134/42 |
| 6,680,289 | B1 * | 1/2004 | Woo et al. | 510/470 |
| 6,713,075 | B2 * | 3/2004 | Bekele | 424/401 |
| 6,824,650 | B2 * | 11/2004 | Lindsay et al. | 162/168.2 |
| 7,141,077 | B2 * | 11/2006 | Detering et al. | 8/137 |
| 7,541,409 | B2 * | 6/2009 | Grimm et al. | 525/328.2 |
| 7,754,197 | B2 * | 7/2010 | Wu et al. | 424/76.2 |
| 8,178,081 | B2 | 5/2012 | Wu et al. | |
| 2002/0176878 | A1 * | 11/2002 | Bekele | 424/401 |
| 2005/0239974 | A1 * | 10/2005 | Grimm et al. | 525/430 |
| 2006/0287219 | A1 | 12/2006 | Dykstra et al. | |
| 2008/0164439 | A1 | 7/2008 | Fang et al. | |
| 2008/0194454 | A1 | 8/2008 | Morgan et al. | |
| 2010/0197554 | A1 * | 8/2010 | Koyuncu et al. | 510/236 |
| 2011/0070182 | A1 | 3/2011 | Williams et al. | |

FOREIGN PATENT DOCUMENTS

| | | |
|---|---|---|
| CA | 1173631 A | 9/1984 |
| JP | A-2001-353208 | 12/2001 |
| JP | A-2006-149892 | 6/2006 |
| JP | A-2006-149893 | 6/2006 |
| JP | A-2007-332130 | 12/2007 |
| JP | A-2010-047688 | 3/2010 |
| WO | WO 9742285 A1 * | 11/1997 |
| WO | WO 02094329 A1 * | 11/2002 |
| WO | WO 2011/084463 A1 | 7/2011 |

OTHER PUBLICATIONS

Illergard J. Development of new bacteria-reducing surfaces. KTH Royal Institute of Technology (2009), Thesis:1-36.*
PCT Search Report for International application No. PCT/US2012/020886, dated Apr. 24, 2012, containing 13 pages.

* cited by examiner

Primary Examiner — Robert A Wax
Assistant Examiner — Olga V Tcherkasskaya
(74) Attorney, Agent, or Firm — Abbey A. Lopez; Amy I. Ahn-Roll

(57) ABSTRACT

Compositions comprising hydrophobically modified malodor control polymers and methods thereof are provided. In some embodiments, the composition comprises a malodor control polymer, a malodor counteractant comprising a perfume, an aqueous carrier, and a ph of about 6 to about 8. Such compositions may be used to reduce or neutralize malodors on surfaces or in the air.

13 Claims, No Drawings

COMPOSITIONS COMPRISING HYDROPHOBICALLY MODIFIED MALODOR CONTROL POLYMERS

FIELD OF THE INVENTION

The present invention relates to compositions comprising hydrophobically modified malodor control polymers and methods thereof.

BACKGROUND OF THE INVENTION

Products for reducing or masking malodors are currently available and are widely described in patent literature. These products may be designed to work specifically in air, on fabrics, or on other surfaces. However, not all malodors are effectively controlled by products in the market. Amine-based malodors such as fish and urine malodors and sulfur-based malodors such as garlic, onion, foot, and fecal malodors are difficult to combat. Further, the time required for a product to noticeably combat malodors may create consumer doubt as to a product's efficacy on malodors. For example, a consumer may leave the treated space before the product begins to noticeably reduce the malodors. Even further, certain compositions may cause fabrics on surrounding surfaces to turn yellow or brown under natural light and/or make fabrics susceptible to soiling, particularly compositions that contain certain types or amounts of aldehydes and/or surfactants. The difficulty in overcoming a broad range of malodors has spawned a diverse assortment of products to neutralize, mask, or contain malodors.

There remains a continuing need for a malodor control composition that neutralizes a broad range of malodors, including amine-based and sulfur-based malodors, while not overpowering malodors with an overwhelming perfume and while not soiling and staining fabrics.

SUMMARY OF THE INVENTION

According to one embodiment of the present invention, there is provided a composition for reducing malodor comprising: (a) an effective amount of a malodor control polymer having the structure (I):

$$P(R)x \qquad (I)$$

wherein P is selected from the group consisting of: partially hydrolyzed polyvinylamines (PVams), polyethyleneimines (PEIs), polyamidoamines (PAMams), polyallyamines (PAams), polyetheramines (PEams), and mixtures thereof; x is degree of substitution of the amine sites on the polymer and is less than 100%; and R is a C2 to C26 alkyl or alkenyl; (b) a malodor counteractant comprising a perfume material; and (c) an aqueous carrier; wherein said composition comprises a pH of about 6 to about 8.

According to another embodiment of the present invention, there is provided a composition for reducing malodor comprising: (a) an effective amount of a malodor control polymer having the structure (I):

$$P(R)x \qquad (I)$$

wherein P is selected from the group consisting of: PAams, PEams, and mixtures thereof; x is degree of substitution of the amine sites on the polymer and is less than 100%; and R is a C2 to C12 and C16 to C26 alkyl or alkenyl; (b) a malodor counteractant comprising a perfume material; and (c) an aqueous carrier; wherein said composition comprises a pH of about 5 to about 10.

According to yet another embodiment of the present invention, there is provided a composition for reducing malodor comprising: (a) an effective amount of a malodor control polymer having the structure (I):

$$P(R)x \qquad (I)$$

wherein P is selected from the group consisting of: partially hydrolyzed PVams, PEIs, PAMams, PAams, PEams, and mixtures thereof; x is degree of substitution of the amine sites on the polymer and is less than 100%; and R is a C2 to C26 alkyl or alkenyl; (b) a malodor counteractant comprising a perfume material; (c) an aqueous carrier; and (d) cyclodextrin; wherein said composition comprises a pH of about 6 to about 8.

According to yet another embodiment of the present invention, there is provided a method of reducing malodor comprising the steps of: (a) providing a freshening composition comprising:

an effective amount of a malodor control polymer having the structure (I):

$$P(R)x \qquad (I)$$

wherein P is selected from the group consisting of: partially hydrolyzed PVams, PEIs, PAMams, PAams, PEams, and mixtures thereof; x is degree of substitution of the amine sites on the polymer and is less than 100%; and R is a C2 to C26 alkyl or alkenyl; a malodor counteractant comprising a perfume material; and an aqueous carrier; wherein said composition comprises a pH of about 6 to about 8; and (b) dispersing an effective amount of said composition on an inanimate surface or in the air.

DETAILED DESCRIPTION OF THE INVENTION

The composition of the present invention is designed to deliver genuine malodor reduction and not function merely by using perfume to cover up or mask odors. A genuine malodor reduction provides a sensory and analytically measurable (e.g. gas chromatograph) malodor reduction. Malodors may include odors from food such as fish, onion, and garlic; odors from grease, body, mold/mildew, smoke, pet urine, sewage; and bathroom based odors. Thus, if the composition delivers a genuine malodor reduction, the composition will neutralize malodors in the air, on fabrics, and/or on other surfaces.

"Neutralize" or "neutralization" as used herein means chemically reacting with malodor components (e.g. the reaction of primary amines with aldehydes to form imines, reductive alkylation of amines, protonation and deprotonation of amines, polymerization or de-polymerization); or suppressing the volatility of malodorous components such that other parts of the composition may react (e.g. acid-base neutralization); or physically entrapping odorous molecules such that they are not re-released into the air (e.g. cyclodextrin inclusion complexes as described herein).

The composition may also act as a barrier to prevent malodors from adhering to or penetrating a surface.

I. Composition

The composition for reducing malodor comprises an effective amount of a malodor control polymer, a malodor counteractant comprising a perfume material, and an aqueous carrier.

In one embodiment, the composition may be free of ingredients that soil or stain fabrics treated with or surrounding the treated surface. In such embodiments, the total amount of surfactants (e.g. solubilizer, wetting agent) in the composition is from 0% to about 3% or no more than about 3%, alternatively from 0% to about 1% or no more than about 1%, alternatively from 0% to about 0.9% or no more than about 0.9%, alternatively from 0% to about 0.7 or no more than 0.7%, alternatively from 0% to about 0.5% or no more than about 0.5%, alternatively from 0% to about 0.3% or no more than about 0.3%, by weight of the composition. Compositions with higher concentrations may make fabrics susceptible to soiling and/or leave unacceptable visible stains on fabrics as the solution evaporates.

A. Hydrophobically Modified Malodor Control Polymers

The composition of the present invention includes a hydrophobically modified malodor control polymer (HMP). A HMP is formed from a polyamine polymer having a primary, secondary, and/or tertiary amine group that is modified with a hydrophobic group such as an alkyl, alkenyl, alkyloxide, or amide. Although the amine group has been modified, a HMP has at least one free and unmodified primary, secondary, and/or tertiary amine group, to react with malodorous components. Not wishing to be bound by theory, hydrophobic modification may increase a polymer's affinity for hydrophobic odors, thus enabling interactions between the odor molecules and active amine sites. In turn, HMPs may improve the breadth of malodor removal efficacy A HMP of the present invention has the general formula (I):

$$P(R)x \qquad (I)$$

wherein:

P is a polyamine polymer;

R is a C2 to C26 hydrophobic group; and x is the total degree of substitution, which is less than 100%, of amine sites on the polymer.

1. Polyamine Polymer

HMPs may include a polyamine polymer backbone that can be either linear or cyclic. HMPs can also comprise polyamine branching chains. The polyamine polymer has a general formula (I1):

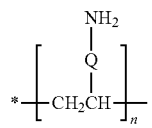

where Q is an integer having values between 0-3.

Non-limiting examples of polyamine polymers include polyvinylamines (PVams), polyethyleneimines (PEIs) that are linear or branched, polyamidoamines (PAMams), polyallyamines (PAams), polyetheramines (PEams) or other nitrogen containing polymers, such as lysine, or mixtures of these nitrogen containing polymers.

a. PVams

In one embodiment, the HMP includes a PVam backbone. A PVam is a linear polymer with pendent, primary amine groups directly linked to the main chain of alternating carbons. PVams are manufactured from hydrolysis of poly(N-vinylformamide) (PVNF) which results in the conversion of formamide units to amino groups as described by the following formula (I1a):

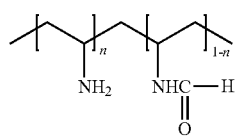

where n is a number from 0.1 to 0.99 depending on the degree of hydrolysis. For instance, in 95% hydrolyzed PVam, n will be 0.95 while 5% of the polymer will have vinylformamide units.

PVams may be partially hydrolyzed meaning that 1% to 99%, alternatively 30% to 99%, alternatively 50% to 99%, alternatively 70% to 99%, alternatively 80% to 99%, alternatively 85% to 99%, alternatively 90% to 99%, alternatively 95% to 99%, alternatively 97% to 99%, alternatively 99% of the PVam is hydrolyzed. It has been found that high degree of hydrolysis of PVam increases the resulting polymer's ability to mitigate the odors.

PVams that can be hydrolyzed may have an average molecular weight (MW) of 5,000 to 350,000 Daltons. Suitable hydrolyzed PVams are commercially available from BASF. Some examples include Lupamin™ 9095, 9030, 5095, and 1595.

Such hydrolyzed PVams may then be hydrophobic ally modified. Hydrophobic modification, as described below may further improve malodor removal efficacy.

b. Polyalkylenimine/PEIs

In another embodiment, the HMP includes a polyalkylenimine backbone. Polyalkylenimines include PEIs and polypropylenimines as well as the C4-C12 alkylenimines.

PEI is a suitable polyalkylenimine. The chemical structure of a PEI follows a simple principle: one amine function and two carbons. PEIs have the following general formula (I1b):

$$-(CH2\text{-}CH2\text{-}NH)n\text{-} \qquad (I1b):$$

where n=10-105

PEIs constitute a large family of water-soluble polyamines of varying molecular weight, structure, and degree of modification. They may act as weak bases and may exhibit a cationic character depending on the extent of protonation driven by pH.

PEIs are produced by the ring-opening cationic polymerization of ethyleneimine as shown below.

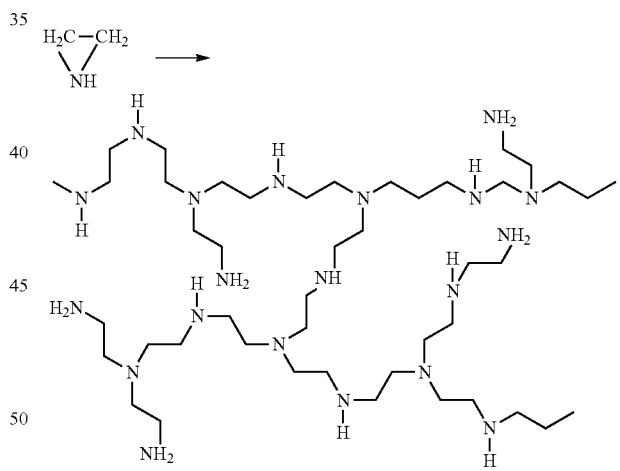

PEIs are believed to be highly branched containing primary, secondary, and tertiary amine groups in the ratio of about 1:2:1. PEIs may comprise a primary amine range from about 30% to about 40%, alternatively from about 32% to about 38%, alternatively from about 34% to about 36%. PEIs may comprise a secondary amine range from about 30% to about 40%, alternatively from about 32% to about 38%, alternatively from about 34% to about 36%. PEIs may comprise a tertiary amine range from about 25% to about 35%, alternatively from about 27% to about 33%, alternatively from about 29% to about 31%.

Other routes of synthesis may lead to products with a modified branched chain structure or even to linear chain PEIs. Linear PEIs contain amine sites in the main chain while the branched PEIs contain amines on the main and side chains. Below is an example of a linear PEI

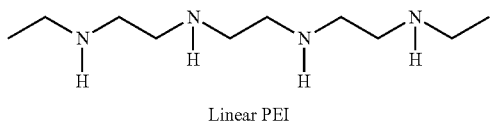

Linear PEI

The composition of the present invention may comprise PEIs having a MW of about 800 to about 2,000,000 Daltons, alternatively about 1,000 to about 2,000,000 Daltons, alternatively about 1,200 to about 25,000 Daltons, alternatively about 1,300 to about 25,000 Daltons, alternatively about 2,000 to about 25,000 Daltons, alternatively about 10,000 to about 2,000,000 Daltons, alternatively about 25,000 to about 2,000,000 Daltons, alternatively about 25,000 Daltons.

In one embodiment, the PEI may have a specific gravity of 1.05 and/or an amine value of 18 (mmol/g, solid). For clarity, such specific gravity and/or amine value of the PEI describes the PEI before it is modified or added as part of an aqueous composition. One skilled in the art will appreciate, for example, the primary and secondary amino groups may react with other components of the composition.

Exemplary PEIs include those that are commercially available under the tradename Lupasol® from BASF or the tradename Epomine™ from Nippon Shokubia.

In some embodiments, less than 100% of the active amine sites are substituted with hydrophobic functional groups, alternatively about 0.5% to about 90%, alternatively about 0.5% to about 80%, alternatively about 0.5% to about 70%, alternatively about 0.5% to about 60%, alternatively about 0.5% to about 50%, alternatively about 0.5% to about 40%, alternatively about 0.5% to about 35%, alternatively about 0.5% to about 30%, alternatively about 1% to about 30%, alternatively about alternatively about 1% to about 25%, alternatively about 1% to about 20%, alternatively about 5% to about 20%, alternatively about 10% to about 30%, alternatively about 20% to about 30%, alternatively about 20% of the active amine sites are substituted with hydrophobic functional groups. When a PEI has active amine sites that are fully substituted with hydrophobic functional groups, such hydrophobically modified PEI may have no activity for malodor control.

c. PAMams

In another embodiment, the HMP includes a PAMam backbone. PAMams are polymers whose backbone chain contains both amino functionalities (NH) and amide functionalities (NH—C(O)). PAMams also contain primary amine groups and/or carboxyl groups at the termini of polymer chain. The general structure of a PAMam is below (I1c):

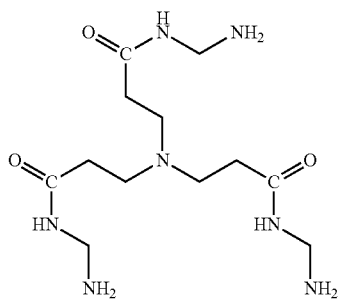

d. PAams

In another embodiment, the HMP includes a PAam backbone. PAams are prepared from polymerization of allyamine—$C_3H_5NH2$. Unlike PEIs, they contain only primary amino groups that are linked to the side chains. The general formula for a PAAm is shown below (I1d):

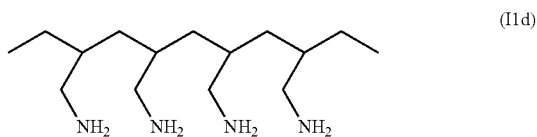

e. PEams

In yet another embodiment, the HMP includes a PEam backbone. PEams contain a primary amino groups attached to the end of a polyether backbone. The polyether backbone may be based on propylene oxide (PO), ethylene oxide (EO), or mixed PO/EO. The general formula for a PEam is shown below (I1e):

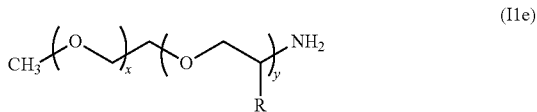

R = H for (EO) or CH3 for (PO)

These so-called monoamines, M-series, are commercially available from Hunstman under the tradename Jeffamine® monoamines. In another embodiment, the HMP includes a PEam backbone having diamines as shown below (I1f):

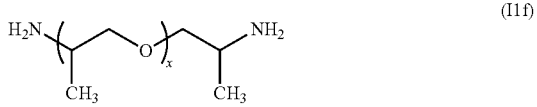

Diamines are commercially available from Hunstman under the tradename Jeffamine® diamines (e.g. D, ED, and EDR series). The HMP may also include a PEam backbone having triamines (e.g. Jeffamine® triamine T-series).

2. Other Polymer Units

HMPs may include a copolymer of nitrogen-containing polymers having the formula (I2):

where Q is an integer having values between 0-3 and V is a co-monomer.

Non-limiting examples of (I2) unmodified polymers include vinylamides, vinyl pyrrolidone, vinylimidazole, vinylesters, vinylalcohols, and mixtures thereof.

3. Hydrophobic Group

The hydrophobic group of the HMP may be linear, branched, or cyclic alkyl, hydroxyalkyl, alkenyl, hydroxyalkenyl, alkyl carboxyl, alkyloxide, alkanediyl, amide, or aryl. In some embodiments, the hydrophobic group is a C2 to C26, alternatively a C2 to C12, alternatively a C2 to C10, alternatively a C4 to C10, alternatively a C16 to C26, alternatively a C6. Where cyclodextrin is included in a formulation, it may be desirous to use a HMP that has been modified with a C2 to C10 alkyl group, alternatively a C16-C26 alkyl group, alternatively a C6 alkyl group, since such alkyl groups are cyclodextrin compatible.

4. Hydrophobic Modification

The polyamine backbones are hydrophobically modified in such a manner that at least one nitrogen, alternatively each nitrogen, of the polyamine chain is thereafter described in terms of a unit that is substituted, quaternized, oxidized, or combinations thereof.

There are many ways of hydrophobically modifying polyamine polymers. Generally, the modification is one directed to the primary, secondary, and/or tertiary amines of the polymer. By reacting the unmodified polyamine backbone with appropriate reagents, one can render the polyamine polymer hydrophobic, thereby increasing efficacy for malodor removal. The following are non limiting examples of the ways to prepare the HMPs disclosed herein.

a. Alkoxylation

The reaction of polyamine polymer with an epoxide containing hydrocarbons (R) results in substitution of one or more nitrogen moities on the polymer.

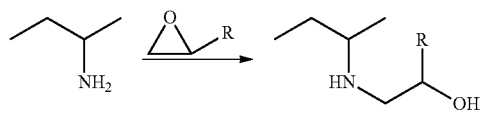

wherein R>C2.

Non-limiting example of such hydrocarbons include C2-C26 chain that is substituted or unsubstituted, branched or unbranched. For example, a reaction of dodeceneoxide with PEI polymer results in C6-HMP disclosed herein having a structure shown below.

natively, hydroxyl groups can be substituted by further reacting the alkoxylated polymers as described in subparagraph c below.

b. Amidation

Reaction of polyamine polymers with amide-forming reagents such as anhydrides, lactones, isocyanates, or carboxylic acids results in substitution of one or more nitrogen moieties on the polymer rendering hydrophobic character. Prior to amidation, one can begin with partial substitution of amine sites with EO or PO and then carry out amidation on the remaining amine moieties. Reaction of anhydrides with polyamine polymers leads to the formation of amide units of the polymer by partial substitution of the primary/secondary amine sites. Non-limiting examples include non-cyclic carboxylic anhydrides such as acetic anhydride or cyclic carboxylic anhydrides such as maleic anhydride, succinic anhydride or phthalic anhydride. For example, the reaction of a polyamine with acetic anhydride introduces amide units onto the polymer.

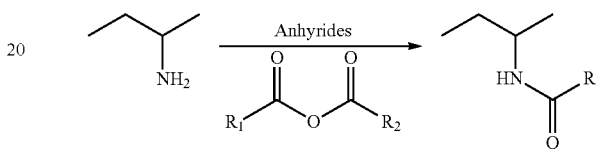

wherein R>C2.

On the other hand, the reaction of polyamine polymer with cyclic anhydrides introduces amido acid units onto the polymer.

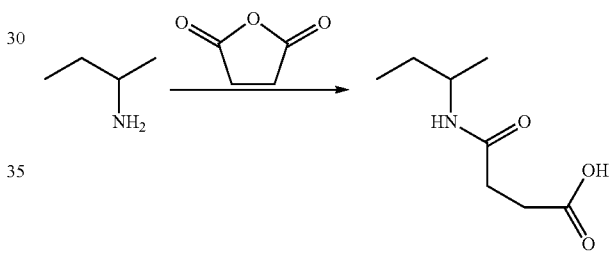

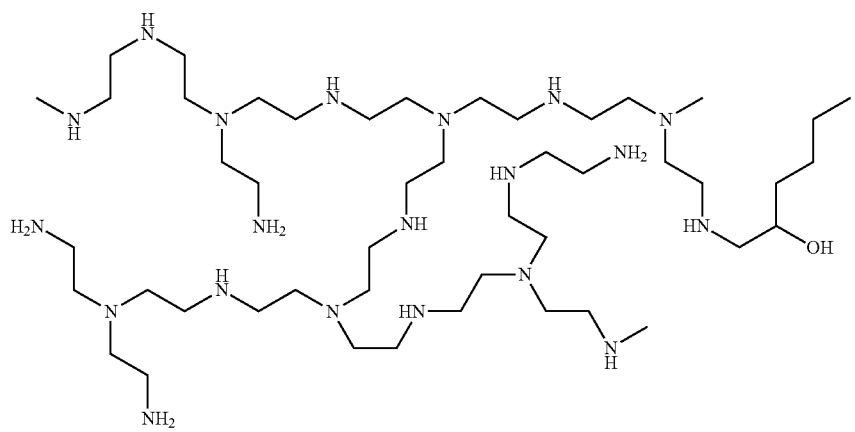 [SMILES: CCCCC(O)CNCCN(C)CCNCCN(CCNCCN(CCN)CCNCCNC)CCNCCN(CCNCCN(CCN)CCN)CCNCCN(CCNC)CCNCCN]

Alternatively, one can modify the base polymer by reacting with EO first and then finish it by alkylation. Additional modifications might also include capping the modified polymer with EO groups if more water solubility is desired. Alternatively, one can modify the base polymer by reacting with EO first and then finish it by alkylation. Additional modifications might also include capping the modified polymer with EO groups if more water solubility is desired. Alternatively, More hydrophobically modified derivatives can be prepared by the use of cyclic anhydrides such as alkylene succinic anhydrides, dodecenyl succinic anhydride or polyisobutane succinic anhydride.

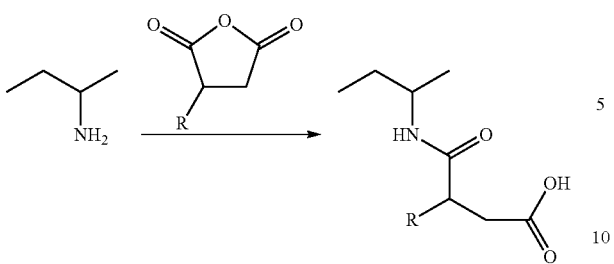

wherein R>C2.

Polyamine polymers containing hydroxyl-terminated polyamido units can be prepared by reacting the polymers with lactones. The use of more hydrophobic alkyl substituted lactones may introduce more hydrophobicity. Optionally, hydroxyl-end groups can be further substituted with functional groups as described in the subparagraph c below.

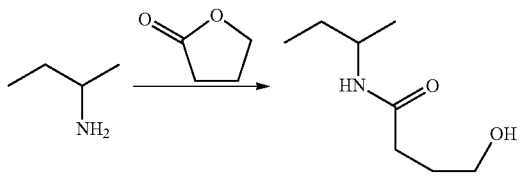

Isocyanate reactions with polyamine polymers result in the formation of urea derivatives as shown below.

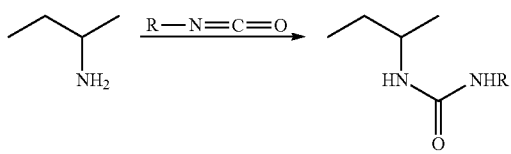

wherein R>C2.

c. Alkoxylation Followed by Substitution of Hydroxyl Groups

Additional functional groups can be covalently bonded to an OH group on the alkoxylated polyamine polymers ("x" in formula (I)). This can be achieved by further reacting the alkoxylated polymers with bifunctional compounds such as epihalohydrins such as epichlorohydrin, 2-halo acid halides, isocyanataes or disocyanates such as trimethylhexane diisocyanate, or cyclic carboxylic anhydrides such as maleic anhydride or phthalic anhydride. For example, the reaction of alkoxylated PEI with isocyanates yields:

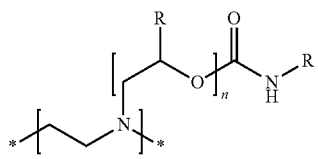

wherein R>C2.

Reaction products of alkoxylated PEI and alk(en)ylsuccinic anhydrides yield

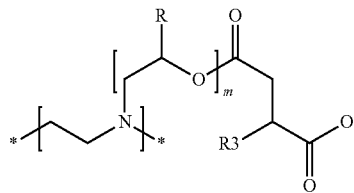

wherein R>C2.

All these HMPs disclosed herein can be optionally capped with hydrophilic groups, such as EO, to render water solubility if necessary.

In some embodiments, about 0.5% to about 90% of the amine groups on the entire unmodified polyamine polymer may be substituted with a hydrophobic group, alternatively about 0.5% to about 80%, alternatively about 0.5% to about 70%, alternatively about 0.5% to about 60%, alternatively about 0.5% to about 50%, alternatively about 0.5% to about 40%, alternatively about 0.5% to about 35%, alternatively about 0.5% to about 30%, alternatively about 1% to about 30%, alternatively about alternatively about 1% to about 25%, alternatively about 1% to about 20%, alternatively about 5% to about 20%, alternatively about 10% to about 30%, alternatively about 20% to about 30%, alternatively about 20% of the amine groups on the entire unmodified polyamine polymer may be substituted with a hydrophobic group. The level of substitution of the amine units can be as low as 0.01 mol percent of the theoretical maximum where all primary, secondary, and/or tertiary amine units have been replaced.

HMPs for use herein may have a MW from about 150 to about $2*10^6$, alternatively from about 400 to about $10^6$, alternatively from about 5000 to about $10^6$.

Malodor control polymers suitable for use in the present invention are water-soluble or dispersible. In some embodiments, the primary, secondary, and/or tertiary amines of the polyamine chain are partially substituted rendering hydrophobicity while maintaining the desired water solubility. The minimum solubility index of a HMP may be about 2% (i.e. 2 g/100 ml of water). A suitable HMP for an aqueous fabric refresher formulation may have a water solubility percentage of greater than about 0.5% to 100%, alternatively greater than about 5%, alternatively greater than about 10%, alternatively greater than about 20%.

The water solubility index can be determined by the following test.

Water Solubility

This test illustrates the benchmarking ambient temperature water solubility of HMPs against beta-cyclodextrin (1.8 g/100 ml) and hydroxypropyl modified beta cyclodextrin (60+ g/100 ml). 1% water solubility is used as a screening criteria for HMPs suitable for use in aqueous fabric refresher formulations.

Room temperature equilibrium water solubility of polymers may be determined by adding weighed quantities of polymers into 100 ml of deionized water and allowing the added polymers to completely dissolve. This process is repeated until the added polymers are no longer soluble. Equilibrium water solubility is then calculated based on how much polymer is dissolved in 100 ml water.

| Polymer | Equilibrium Water Solubility (g/100 ml water at 25° C.) |
| --- | --- |
| Lupasol G100 (PEI 5,000) | miscible at all levels (70+) |
| C6 modified PEI 1800 (0.25 C6/NH) | 30+ |
| Dodecene oxide modified PEI5,000 (0.1 dodecene oxide/NH) | ~24 |
| Dodecene oxide modified PEI5,000 (0.2 dodecene oxide/NH) | ~4 |
| Dodecene oxide modified PEI5,000 (0.5 dodecene oxide/NH) | <0.1 |
| Dodecene oxide modified PEI25,000 (0.1 dodecene oxide/NH) | ~21 |
| Dodecene oxide modified PEI25,000 (0.2 dodecene oxide/NH) | <0.1 |
| Dodecene oxide and EO modified PEI25,000 (0.8 EO and 0.2 dodecene oxide/NH) | ~6 |

When the polymer is not water soluble (e.g. less than 0.05%), capping with a hydrophilic molecule may be desired to assist with water solubility. Suitable hydrophilic molecules include EO or other suitable hydrophilic functional groups.

Suitable levels of HMPS in the present composition are from about 0.01% to about 10%, alternatively from about 0.01% to about 2%, alternatively from about 0.01% to about 1%, alternatively from about 0.01% to about 0.8%, alternatively from about 0.01% to about 0.6%, alternatively from about 0.01% to about 0.1%, alternatively from about 0.01% to about 0.07%, alternatively about 0.07%, alternatively about 0.5%, by weight of the composition. Compositions with higher amount of HMPs may make fabrics susceptible to soiling and/or leave unacceptable visible stains on fabrics as the composition evaporates off of the fabric.

Suitable HMPs include partially hydrolyzed hydrophobically modified PVams, hydrophobically modified PEIs, hydrophobically modified PAMams, hydrophobically modified PAams, hydrophobically modified PEams, and mixtures thereof.

B. Malodor Counteractants

The composition may utilize one or more malodor counteractants. Malodor counteractants may include components which lower the vapor pressure of odorous compounds, solubilize malodor compounds, physically entrap odors (e.g. flocculate or encapsulate), physically bind odors, or physically repel odors from binding to inanimate surfaces.

1. Aliphatic Aldehydes

In one embodiment, the composition comprises a perfume material having one or more fabric-safe, non-yellowing aliphatic aldehyde. Aliphatic aldehydes react with amine odors, such as fish and cigarette odors. When used in combination with the HMP, the composition may neutralize a broader range of malodor causing materials which, in turn, further reduces malodors in the air or on inanimate surfaces. Certain types of aldehydes that predominately comprise a straight chain aliphatic backbone will not discolor fabrics, unlike products that utilize types of aldehydes that contain multiple double bonds and benzene rings. The following table illustrates the selection of aldehydes to avoid fabric yellowing.

| Aldehyde Solution Tested | Fadometer Test on treated Fabric (0.75 grams of product are pipetted onto a 4 inch × 4 inch (10 cm × 10 cm) swatch which is then subjected to 5 hours of exposure to simulated sunlight using a SUNTEST CPS+ model Fadometer supplied by Atlas, Chicago, Illinois, USA. |
| --- | --- |
| Control-untreated fabric swatch | No yellowing |
| 1000 ppm amylic cinnamic aldehyde (aromatic) | Yellowish brown |
| 1000 ppm citronellal (aromatic) | Yellowish brown |
| 1000 ppm citral aldehyde (aliphatic) | No yellowing |
| 1000 ppm lauric aldehyde (aliphatic) | No yellowing |

Examples of suitable aliphatic aldehydes are R—COH where R is saturated $C_7$ to $C_{22}$ linear and/or branched with no more than two double bonds. Examples of suitable aliphatic aldehydes are bourgeonal, citral, citronellyl oxyacetaldehyde, cymal, decyl aldehyde, helional, hexyl cinnamic aldehyde, lauric aldehyde, ligustral, lyral, melonal, methyl dihydro jasmonate, methyl nonyl acetaldehyde, methyl phenyl carbinyl acetate, nonyl aldehyde, octyl aldehyde, oxane, P. T. bucinal, polysantol, rhubafuran, tripal, or mixtures thereof.

In one embodiment, the composition includes at least one aliphatic aldehyde selected from the group consisting of: bourgeonal, citral, citronellyl oxyacetaldehyde, cymal, decyl aldehyde, helional, hexyl cinnamic aldehyde, lauric aldehyde, ligustral, lyral, melonal, methyl dihydro jasmonate, methyl nonyl acetaldehyde, methyl phenyl carbinyl acetate, nonyl aldehyde, 2,6-nonadien-1-al, octyl aldehyde, oxane, P.T. bucinal, polysantol, rhubafuran, tripal, and mixtures thereof.

In another embodiment, the composition includes at least one aliphatic aldehyde selected from the group consisting of: bourgeonal, cymal, hexyl cinnamic aldehyde, methyl dihydro jasmonate, methyl nonyl acetaldehyde, P.T. bucinal, and mixtures thereof.

The aliphatic aldehydes may be present in an amount from about 0.001% to about 10%, alternatively from about 0.001% to about 5%, alternatively from about 0.01% to about 1%, alternatively from about 0.02% to about 1%, alternatively from about 0.02% to about 0.5%, alternatively from about 0.02% to about 0.06%, alternatively about 0.06%, by weight of the composition.

In addition to aliphatic aldehydes, the composition may also include perfume materials for their scent experience including enones, ketones, ionones including ionone alpha, ionone beta, ionone gamma methyl, or mixtures thereof. Suitable perfume materials are discussed in U.S. Pat. No. 5,714,137. The composition may contain an effective amount of perfume to provide a freshening fragrance when first sprayed, some lingering fragrance, and some extra fragrance to be released upon fabric rewetting. It may be desirable for the aliphatic aldehydes to have virtually no negative impact on the desired perfume character.

Certain malodor counteractants may be odoriferous and negatively impact the overall character of the fragrance. In this case, a perfume/malodor counteractant premix is formed such that the perfume raw materials used are selected to neutralize any odor of the malodor counteractants. This odor neutralized premix can then be added to a parent perfume mixture without affecting the character of the parent fragrance. This permits the malodor counteractants to be used broadly with a large variety of fragrance types.

The following are non-limiting examples of perfume mixtures that include fabric-safe malodor counteractants.

(1) Pine

| Material Name | Amount |
|---|---|
| Rosemary | 10.00 |
| Spike Lavender | 10.00 |
| Lavandin Grosso | 5.00 |
| Spruce (conf.-manh) | 5.00 |
| Camphor Gum | 5.00 |
| Melonal | 0.30 |
| Eucalyptol | 15.00 |
| Iso Menthone | 15.00 |
| Iso Bornyl Acetate | 21.70 |
| Ionone Beta | 8.00 |
| Iso E Super | 5.00 |
| | 100.00 |

(2) Ozonic

| Material Name | Amount |
|---|---|
| Xi Aldehyde | 8.00 |
| 2'6 Nonadienol 10% In Dpg | 5.00 |
| Helional | 13.00 |
| Hydroxycitronellal | 11.50 |
| Calone 1951 | 0.50 |
| 2'6-Nonadien-1-al/10% In Dpg | 5.00 |
| Lyral | 20.00 |
| Melonal | 1.00 |
| Iso Menthone | 10.00 |
| Floralozone | 10.00 |
| Bourgeonal | 10.00 |
| Delta Muscenone 962191 | 1.00 |
| Habanolide 100% | 5.00 |
| | 100.00 |

(3) Fruity

| Material Name | Amount |
|---|---|
| Fruitate | 5.00 |
| Orange Terpenes | 13.00 |
| Ethyl Acetoacetate | 3.00 |
| 2'6 Nonadienol 10% In Dpg | 1.00 |
| Ethyl Acetate | 3.00 |
| Benzaldehyde | 2.00 |
| Prenyl Acetate | 8.00 |
| Benzyl Acetate | 15.00 |
| 2'6-Nonadien-1-al/10% In Dpg | 1.00 |
| Ethyl-2-methyl Butyrate | 8.00 |
| Amyl Acetate | 3.00 |
| Cis 3 Hexenyl Acetate | 3.00 |
| Methyl Dihydro Jasmonate | 10.00 |
| Ligustral | 5.00 |
| Melonal | 1.00 |
| Ethyl 2 Methyl Pentanoate | 8.00 |
| Hexyl Acetate | 8.00 |
| Habanolide 100% | 3.00 |
| | 100.00 |

(4) Citrus

| Material Name | Amount |
|---|---|
| Orange Terpenes | 20.00 |
| Lemon Terpenes X5 Fold | 20.00 |
| Lime Oil Cf-8-1285-1 (conf.-berje) | 10.00 |
| Grapefruit Phase C-Ref. N*12245 | 20.00 |
| Italian Orange Phase Oil | 22.90 |
| Delta Muscenone 962191 | 0.50 |
| Oxane | 0.30 |
| Iso Menthone | 1.00 |
| Rhubafuran | 0.30 |
| Habanolide 100% | 5.00 |
| | 100.00 |

(5) Floral

| Material Name | Amount |
|---|---|
| Spike Lavender | 5.00 |
| Rosemary | 5.00 |
| Helional | 10.00 |
| Hydroxycitronellal | 10.00 |
| Benzyl Acetate | 9.30 |
| Lyral | 20.00 |
| Ligustral | 2.00 |
| Melonal | 0.20 |
| Eucalyptol | 2.00 |
| Iso Menthone | 8.00 |
| Bourgeonal | 20.00 |
| Undecavertol | 3.00 |
| Delta Muscenone 962191 | 0.50 |
| Habanolide 100% | 5.00 |
| | 100.00 |

In certain cases, fabrics that are laundered will have residual brighteners deposited from detergents with which they are washed. Therefore, it may be desirable for the malodor counteractant to be compatible with brighteners so that the composition will not discolor any fabrics with which it comes into contact. A number of the examples above are compatible with brighteners.

2. Low Molecular Weight Polyols

Low molecular weight polyols with relatively high boiling points, as compared to water, such as ethylene glycol, diethylene glycol, triethylene glycol, propylene glycol, dipropylene glycol, and/or glycerine may be utilized as a malodor counteractant for improving odor neutralization of the freshening composition of the present invention. Some polyols, e.g., dipropylene glycol, are also useful to facilitate the solubilization of some perfume ingredients in the composition of the present invention.

The glycol used in the composition of the present invention may be glycerine, ethylene glycol, propylene glycol, dipropylene glycol, polyethylene glycol, propylene glycol methyl ether, propylene glycol phenyl ether, propylene glycol methyl ether acetate, propylene glycol n-butyl ether, dipropylene glycol n-butyl ether, dipropylene glycol n-propyl ether, ethylene glycole phenyl ether, diethylene glycol n-butyl ether, dipropylene glycol n-butyl ether, diethylene glycol mono butyl ether, dipropylene glycol methyl ether, tripropylene glycol methyl ether, tripropylene glycol n-butyl ether, other glycol ethers, or mixtures thereof. In one embodiment, the glycol used is ethylene glycol, propylene glycol, or mixtures thereof. In another embodiment, the glycol used is diethylene glycol.

Typically, the low molecular weight polyol is added to the composition of the present invention at a level of from about 0.01% to about 5%, by weight of the composition, alternatively from about 0.05% to about 1%, alternatively from about 0.1% to about 0.5%, by weight of the composition. Compositions with higher concentrations may make fabrics susceptible to soiling and/or leave unacceptable visible stains on fabrics as the solution evaporates off of the fabric. The weight ratio of low molecular weight polyol to the HMP is from about 500:1 to about 4:1, alternatively from about 1:100 to about 25:1, alternatively from about 1:50 to about 4:1, alternatively about 4:1.

3. Cyclodextrin

In some embodiments, the composition may include solubilized, water-soluble, uncomplexed cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many perfume molecules can fit into the cavity.

Cyclodextrin molecules are described in U.S. Pat. No. 5,714,137, and U.S. Pat. No. 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the composition. Compositions with higher concentrations can make fabrics susceptible to soiling and/or leave unacceptable visible stains on fabrics as the solution evaporates off of the fabric. The latter is especially a problem on thin, colored, synthetic fabrics. In order to avoid or minimize the occurrence of fabric staining, the fabric may be treated at a level of less than about 5 mg of cyclodextrin per mg of fabric, alternatively less than about 2 mg of cyclodextrin per mg of fabric.

C. Buffering Agent

The composition of the present invention may include a buffering agent which may be a dibasic acid, carboxylic acid, or a dicarboxylic acid like maleic acid. The acid may be sterically stable, and used in this composition solely for maintaining the desired pH. The composition may have a pH from about 6 to about 8, alternatively from about 6 to about 7, alternatively about 7, alternatively about 6.5. In some embodiments, when the HMP is not water soluble, it may be desirable to adjust pH of the freshening composition from about 6 to about 8, alternatively from about 6 to about 7, alternatively about 7, alternatively about 6.5.

Carboxylic acids such as citric acid may act as metal ion chelants and can form metallic salts with low water solubility. As such, in some embodiments, the freshening composition is essentially free of citric acids. The buffer can be alkaline, acidic or neutral.

Other suitable buffering agents for freshening compositions of this invention include biological buffering agents. Some examples are nitrogen-containing materials, sulfonic acid buffers like 3-(N-morpholino)propanesulfonic acid (MOPS) or N-(2-Acetamido)-2-aminoethanesulfonic acid (ACES), which have a near neutral 6.2 to 7.5 pKa and provide adequate buffering capacity at a neutral pH. Other examples are amino acids such as lysine or lower alcohol amines like mono-, di-, and tri-ethanolamine. Other nitrogen-containing buffering agents are tri(hydroxymethyl)amino methane (HOCH2)3CNH3 (TRIS), 2-amino-2-ethyl-1,3-propanediol, 2-amino-2-methyl-propanol, 2-amino-2-methyl-1,3-propanol, disodium glutamate, N-methyldiethanolamide, 2-dimethylamino-2-methylpropanol (DMAMP), 1,3-bis(methylamine)-cyclohexane, 1,3-diamino-propanol N,N'-tetramethyl-1,3-diamino-2-propanol, N,N-bis(2-hydroxyethyl) glycine (bicine) and N-tris(hydroxymethyl)methylglycine (tricine). Mixtures of any of the above are also acceptable.

The compositions may contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

D. Solubilizer

The composition of the present invention may contain a solubilizing aid to solubilize any excess hydrophobic organic materials, particularly any perfume materials, and also optional ingredients (e.g., insect repelling agent, antioxidant, etc.) which can be added to the composition, that are not readily soluble in the composition, to form a clear solution. A suitable solubilizing aid is a surfactant, such as a no-foaming or low-foaming surfactant. Suitable surfactants are nonionic surfactants, cationic surfactants, amphoteric surfactants, zwitterionic surfactants, and mixtures thereof.

In some embodiments, the freshening composition contains nonionic surfactants, cationic surfactants, and mixtures thereof. In one embodiment, the freshening composition contains hydrogenated castor oil. One suitable hydrogenated castor oil that may be used in the present composition is Basophor™, available from BASF.

Compositions containing anionic surfactants and/or detergent surfactants may make fabrics susceptible to soiling and/or leave unacceptable visible stains on fabrics as the solution evaporates off of the fabric. In some embodiments, the freshening composition is free of anionic surfactants and/or detergent surfactants.

When the solubilizing agent is present, it is typically present at a level of from about 0.01% to about 3%, alternatively from about 0.05% to about 1%, alternatively from about 0.01% to about 0.05%, by weight of the freshening composition. Freshening compositions with higher concentrations may make fabrics susceptible to soiling and/or leave unacceptable visible stains on fabrics as the solution evaporates off of the fabric.

E. Antimicrobial Compounds

The composition of the present invention may include an effective amount of a compound for reducing microbes in the air or on inanimate surfaces. Antimicrobial compounds are effective on gram negative and gram positive bacteria and fungi typically found on indoor surfaces that have contacted human skin or pets such as couches, pillows, pet bedding, and carpets. Such microbial species include *Klebsiella pneumoniae, Staphylococcus aureus, Aspergillus niger, Klebsiella pneumoniae, Steptococcus pyogenes, Salmonella choleraesuis, Escherichia coil, Trichophyton mentagrophytes*, and *Pseudomonoas aeruginosa*. In some embodiments, the antimicrobial compounds are also effective on viruses such H1-N1, Rhinovirus, Respiratory Syncytial, Poliovirus Type 1, Rotavirus, Influenza A, Herpes simplex types 1 & 2, Hepatitis A, and Human Coronavirus.

Antimicrobial compounds suitable in the composition of the present invention can be any organic material which will not cause damage to fabric appearance (e.g., discoloration, coloration such as yellowing, bleaching). Water-soluble antimicrobial compounds include organic sulfur compounds, halogenated compounds, cyclic organic nitrogen compounds, low molecular weight aldehydes, quaternary compounds, dehydroacetic acid, phenyl and phenoxy compounds, or mixtures thereof.

In one embodiment, a quaternary compound is used. Examples of commercially available quaternary compounds suitable for use in the composition is Barquat™ available from Lonza Corporation; and didecyl dimethyl ammonium chloride quat under the trade name Bardac® 2250 from Lonza Corporation.

The antimicrobial compound may be present in an amount from about 500 ppm to about 7000 ppm, alternatively about 1000 ppm to about 5000 ppm, alternatively about 1000 ppm to about 3000 ppm, alternatively about 1400 ppm to about 2500 ppm, by weight of the composition.

F. Preservatives

The composition of the present invention may include a preservative. The preservative is included in the present invention in an amount sufficient to prevent spoilage or prevent growth of inadvertently added microorganisms for a specific period of time, but not sufficient enough to contribute to the odor neutralizing performance of the composition. In other words, the preservative is not being used as the antimicrobial compound to kill microorganisms on the surface onto which the composition is deposited in order to eliminate odors produced by microorganisms. Instead, it is being used to prevent spoilage of the composition in order to increase shelf-life.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diaol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives for use in the present invention include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hüls America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative are from about 0.0001% to about 0.5%, alternatively from about 0.0002% to about 0.2%, alternatively from about 0.0003% to about 0.1%, by weight of the composition.

G. Wetting Agent

The composition may include a wetting agent that provides a low surface tension that permits the composition to spread readily and more uniformly on hydrophobic surfaces like polyester and nylon. It has been found that the aqueous solution, without such a wetting agent will not spread satisfactorily. The spreading of the composition also allows it to dry faster, so that the treated material is ready to use sooner. Furthermore, a composition containing a wetting agent may penetrate hydrophobic, oily soil better for improved malodor neutralization. A composition containing a wetting agent may also provide improved "in-wear" electrostatic control. For concentrated compositions, the wetting agent facilitates the dispersion of many actives such as antimicrobial actives and perfumes in the concentrated aqueous compositions.

Non-limiting examples of wetting agents include block copolymers of EO and PO. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Certain of the block polymer surfactant compounds designated Pluronic® and Tetronic® by the BASF-Wyandotte Corp., Wyandotte, Mich., are readily available.

Non-limiting examples of cyclodextrin-compatible wetting agents of this type are described in U.S. Pat. No. 5,714,137 and include the Silwet® surfactants available from Momentive Performance Chemical, Albany, N.Y. Exemplary Silwet surfactants are as follows:

| Name | Average MW |
| --- | --- |
| L-7608 | 600 |
| L-7607 | 1,000 |
| L-77 | 600 |
| L-7605 | 6,000 |
| L-7604 | 4,000 |
| L-7600 | 4,000 |
| L-7657 | 5,000 |
| L-7602 | 3,000; | and mixtures thereof.

H. Aqueous Carrier

The composition of the present invention may include an aqueous carrier. The aqueous carrier which is used may be distilled, deionized, or tap water. Water may be present in any amount for the composition to be an aqueous solution. In some embodiments, water may be present in an amount of about 85% to 99.5%, alternatively about 90% to about 99.5%, alternatively about 92% to about 99.5%, alternatively about 95%, by weight of said freshening composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the composition of the present invention due to the addition of these alcohols to such things as perfumes and as stabilizers for some preservatives, the level of monohydric alcohol may be less than about 6%, alternatively less than about 3%, alternatively less than about 1%, by weight of the composition.

I. Other Optional Ingredients

Adjuvants can be optionally added to the composition herein for their known purposes. Such adjuvants include, but are not limited to, water soluble metallic salts, antistatic agents, insect and moth repelling agents, colorants, antioxidants, and mixtures thereof.

II. Method of Making

The composition can be made in any suitable manner known in the art. All of the ingredients can simply be mixed together. In certain embodiments, it may be desirable to make a concentrated mixture of ingredients and dilute by adding the same to an aqueous carrier before dispersing the composition into the air or on an inanimate surface. In another embodiment, the malodor control polymer may be dispersed in one vessel containing deionized water and ethanol, and low molecular polyols. To this vessel, then, the buffer is added until fully dispersed and visually dissolved. In a separate vessel, the solubilizer and perfume are mixed until homogenous. The solution of solubilizer and perfume are then added to the first mixing vessel, and mixed until homogenous.

III. Methods of Use

The composition of the present invention can be used by dispersing, e.g., by placing an aqueous solution into a dispensing means, such as a spray dispenser and spraying an effective amount into the air or onto the desired surface or article. An effective amount as defined herein means an amount sufficient to neutralize malodor to the point that it is not discernible by the human sense of smell yet not so much as to saturate or create a pool of liquid on an article or surface and so that, when dry, there is no visual deposit readily discernible. Dispersing can be achieved by using a spray device, a roller, a pad, etc.

The present invention encompasses the method of dispersing an effective amount of the composition for reducing malodor onto household surfaces. The household surfaces are selected from the group consisting of countertops, cabinets, walls, floors, toilets, bathroom surfaces, and kitchen surfaces.

The present invention encompasses the method of dispersing a mist of an effective amount of the composition for reducing malodor onto fabric and/or fabric articles. The fabric and/or fabric articles include, but are not limited to, clothes, curtains, drapes, upholstered furniture, carpeting, bed linens, bath linens, tablecloths, sleeping bags, tents, car interior, e.g., car carpet, fabric car seats, etc.

The present invention encompasses the method of dispersing a mist of an effective amount of the composition for reducing malodor impression onto and into shoes wherein the shoes are not sprayed to saturation.

The present invention encompasses the method of dispersing a mist of an effective amount of the composition for reducing malodor impression onto shower curtains.

The present invention relates to the method of dispersing a mist of an effective amount of the composition for reducing malodor impression onto and/or into garbage cans and/or recycling bins.

The present invention relates to the method of dispersing a mist of an effective amount of the composition for reducing malodor impression into the air to neutralize malodor.

The present invention relates to the method of dispersing a mist of an effective amount of the composition for reducing malodor impression into and/or onto major household appliances including, but not limited to, refrigerators, freezers, washing machines, automatic dryers, ovens, microwave ovens, dishwashers, etc., to neutralize malodor.

The present invention relates to the method of dispersing a mist of an effective amount of the composition for reducing malodor impression onto cat litter, pet bedding and pet houses to neutralize malodor.

The present invention relates to the method of dispersing a mist of an effective amount of the composition for reducing malodor impression onto household pets to neutralize malodor.

Examples

Aqueous Composition

Table 1 shows non-limiting examples of compositions according to the present invention. A mixture of water, ethanol, and Silwet L-7600 surfactant is prepared by mixing. The final pH is adjusted to 7 using 30% maleic acid and this solution is used as Control 1. Control 2 and Test Solution I are prepared by adding desired ingredients right before adjusting the pH.

TABLE 1

| Ingredient | Control 1 (Blank) | Control 2 (CD) | Test Solution I (HMP) |
|---|---|---|---|
| Ethanol | 3 | 3 | 3 |
| Surfactant (Silwet L-7600) | 0.1 | 0.1 | 0.1 |
| Hydroxypropyl Beta CD | — | 0.5 | — |
| HMP | — | — | 0.5 |
| Maleic Acid | As needed | As needed | As needed |
| Perfume | — | — | 0.05 |
| Water | Balance | Balance | Balance |
| Total | 100 | 100 | 100 |
| Final pH | 7 | 7 | 7 |

Malodor Control Performance

This example illustrates the malodor efficacy of the HMPs of the present invention. Isovaleric acid was chosen as a chemical surrogate for body odor while butylamine was used as a representative for amine-containing odors such as fish, pet urine, etc. Hydrophobic greasy cooking odors were represented by aldehydes such as nonanal.

5 ml test solution was placed in a GC-MS vial and spiked with 5 microliters of chemical surrogates shown in Table 2. The solutions are first equilibrated at room temperature for 2 hours, then incubated at 35° C. for 30 minutes. The headspace of each vial is finally sampled using a polydimethyl siloxane (PDMS)/Solid-Phase-Micro-Extraction (SPME) fiber and analyzed by GC/MS. The reductions in head space concentrations of odor molecules are measured and the data are normalized to Control. Results are shown in Table 2. Lower numbers denote high levels of malodor molecules present in the solution that are attributed to high malodor control efficacy of polymers. Table 2 demonstrates that HMPs have broader malodor removal efficacy over the Controls and unmodified polymers.

TABLE 2

| Technology | Odor Molecules | | |
|---|---|---|---|
| | Isovaleric Acid (Body) | Butylamine (Fish) | Nonanal (Grease) |
| Control 1 | 1.0 | 1.01 | 1.0 |
| Control 2 (Hydroxypropyl Beta CD) | 0.67 | 1.0 | 0.48 |
| Lupasol WF PEI 25,000 (no hydrophobic modification) | 0.1 | 0.01 | 0.78 |
| 100% ethyleneoxide/ propyleneoxidemodified PEI 600 | 0.77 | 1.0 | 0.87 |
| Lupamin 9000 (PVam) (0% hydrolyzed) | 0.93 | 0.97 | 0.96 |
| Lupamin 9030 (30% hydrolyzed) | 0.61 | 0.06 | 0.05 |
| Lupamin 9095 (95% hydrolyzed) | 0.37 | 0.01 | 0.04 |
| Lupamin 1595 (95% hydrolyzed) | 0.26 | 0.01 | 0.02 |
| 25% C6 modified PEI 1800 (0.25 C6 and 0.75 EO) | 0.02 | 0.01 | 0.37 |

Throughout this specification, components referred to in the singular are to be understood as referring to both a single or plural of such component.

All percentages stated herein are by weight unless otherwise specified.

Every numerical range given throughout this specification will include every narrower numerical range that falls within such broader numerical range, as if such narrower numerical range were all expressly written herein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc.

Further, the dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition for reducing malodor comprising:
   (a) about 0.01% to about 0.8%, by weight of said composition, of a water soluble malodor control polymer having 1% water solubility and having the structure (I):

$$P(R)x \qquad (I)$$

wherein:
   P is a 95% hydrolyzed PVam;
   x is degree of substitution of the amine sites on the polymer and is less than 100%; and
   R is a C2 to C6 alkyl or alkenyl;
   (b) a malodor counteractant comprising a perfume material, said perfume material comprises at least one aliphatic aldehyde present in the amount of about 0.001% to about 5%, by weight of said composition;
   (c) an aqueous carrier; and
   wherein said composition comprises a pH of about 6 to about 8.

2. The composition of claim 1 wherein R is a C4-C6 alkyl or alkenyl.

3. The composition of claim 1 wherein R is a C6 alkyl or alkenyl.

4. The composition of claim 1 wherein said at least one aliphatic aldehyde is present in the amount of about 0.001% to about 1% by total weight of said composition.

5. The composition of claim 1 wherein said at least one aliphatic aldehyde is selected from the group consisting of bourgeonal, citral, citronellyl oxyacetaldehyde, cymal, decyl aldehyde, helional, hexyl cinnamic aldehyde, lauric aldehyde, ligustral, lyral, melonal, methyl dihydro jasmonate, methyl nonyl acetaldehyde, methyl phenyl carbinyl acetate, nonyl aldehyde, 2' 6-nonadien-1-al, octyl aldehyde, oxane, P.T. bucinal, polysantol, rhubafuran, tripal, and mixtures thereof.

6. The composition of claim 1 wherein said composition further comprises a buffering agent selected from the group consisting of carboxylic acid, dicarboxylic acid, N-(2-Acetamido)-2-aminoethanesulfonic acid, and mixtures thereof.

7. The composition of claim 1 wherein said composition comprises a pH of about 7.

8. The composition of claim 1 wherein said composition is free of anionic surfactants.

9. The composition of claim 1 wherein said composition is free of an ingredient that soils or stains a fabric surface.

10. The composition of claim 1 wherein said composition further comprises no more than 3% surfactant by weight of said composition.

11. The composition of claim 1 wherein said composition further comprises no more than 1% surfactant by weight of said composition.

12. The composition of claim 1 wherein said aqueous carrier is present in an amount of 50% to about 99.5%.

13. A method of reducing malodor comprising the steps of:
   a. providing the composition of claim 1;
   b. dispersing an effective amount of said composition on an inanimate surface or in the air.

* * * * *